United States Patent
Rapaport et al.

[11] Patent Number: 6,018,396
[45] Date of Patent: Jan. 25, 2000

[54] GLOSSMETER

[75] Inventors: Erich Rapaport, Tel Aviv; Amos Nussinovitsch, Petach Tikva; Eyal Mey-Tal, Rehovot, all of Israel

[73] Assignee: Yissum Research Development Company of the Hebrew of Jerusalem, Jerusalem, Israel

[21] Appl. No.: 08/930,531

[22] PCT Filed: Apr. 19, 1996

[86] PCT No.: PCT/EP96/01650

§ 371 Date: Feb. 5, 1998

§ 102(e) Date: Feb. 5, 1998

[87] PCT Pub. No.: WO96/33401

PCT Pub. Date: Oct. 24, 1996

[30] Foreign Application Priority Data

Apr. 20, 1995 [IL] Israel ........................................ 113428

[51] Int. Cl.⁷ .................................................. G01N 21/48
[52] U.S. Cl. .................................. 356/446; 35/34; 35/445
[58] Field of Search ..................................... 356/445, 446, 356/371

[56] References Cited

U.S. PATENT DOCUMENTS

| | | | |
|---|---|---|---|
| 3,349,665 | 10/1967 | Grosheim et al. | 88/14 |
| 4,218,144 | 8/1980 | Whitehouse et al. | 356/445 |
| 4,918,321 | 4/1990 | Klenk et al. | 356/445 |
| 5,313,542 | 5/1994 | Castonguay | 385/115 |
| 5,550,632 | 8/1996 | Harata | 356/446 |

FOREIGN PATENT DOCUMENTS

| | | |
|---|---|---|
| 0 383 244 | 8/1990 | European Pat. Off. |
| 2 123 139 | 1/1984 | United Kingdom |

*Primary Examiner*—Robert H. Kim
*Assistant Examiner*—Zandra V. Smith
*Attorney, Agent, or Firm*—Smith, Gambrell & Russell

[57] ABSTRACT

A glossmeter for the determination of the gloss of regular and irregular shaped objects, including objects with curved surfaces. Illumination is at any desired angle of incidence on the object, which angle can be varied at will. Photosensitive elements (15) are provided in an array arranged on an arc (14), which elements face the objects and which receive light reflected and scattered by the objects. Suitable objects are various kinds of fruit, vegetables, rice and any other object where exact surface gloss is of importance.

4 Claims, 2 Drawing Sheets

GLOSSMETER

FIELD OF THE INVENTION

The invention relates to a novel gloss-meter which provides detailed information on the gloss of a given object. It allows measurements which provide detailed Information as regards the entire surface of the object. Amongst others, the novel gloss meter can be used for determining the gloss of irregular objects and also of curved ones.

BACKGROUND OF THE INVENTION

Gloss is a surface attribute causing a shiny or lustrous appearance. It is generally associated with specular reflection by the object. However, specular reflection can vary from one surface to another as follows:

1. The fraction of light reflected in the specular direction.
2. The manner and extent to which light is spread to either side of this specular direction.
3. The change of fractional reflectance as specular angle changes.

There are at least six different visual criteria by which glossiness is ranked (Table 1).

ESTABLISHED METHODS OF MEASURING GLOSS

There exist a variety of methods to measure gloss since different aspects of reflection, need to be measured to duplicate, as closely as possible, the different visual gloss-grading parameters.

The first established method for gloss measurement (Ingersoll, 193.4) was based on the principle that light is polarized in specular reflection, whereas diffusely reflected light, is nonpolarized. The Ingersoll glarimeter had a specular geometry, with incident and viewing angles at 57.5. Gloss was evaluated by a contrast method that, with the use of a polarizing element, "substracted" the specular component from total reflection.

In around 1930, Pfund pointed out that although specular shininess is the basic (objective) evidence of gloss, actual surface glossy appearance (subjective) relates to the contrast between specular shininess and the diffuse light of the surrounding surface area (now called "contrast gloss" or "luster"). If black and white surfaces of the same shininess are visually compared, the black will appear glossier because of the greater contrast between the specular highlight and the black surroundings as compared to that with than white surroundings. Pfund was the first to suggest that more than one method is needed to analyze gloss (Pfund, 1930).

In his investigation of gloss in the early 1930s Hunter used a specular angle of 45°, as did the first photoelectric gloss methods.

But visual evaluation of a large number of samples (primarily paint) eventually demonstrated that the 60° angle provided the best overall estimates (Hunter and Judd, 1939). The 60° method suggested in 1939 was subsequently adopted by the American Society for Testing and Materials (ASTM Method D523). It is widely used for paints, plastics, waxes and floor coverings, and is more widely used than any other gloss test procedure. The old 45° method is now used primarily for glazed ceramics and polyethylene and other plastic films.

Incorporated into ASTM Method D523 in 1951 as alternative procedures were a 20 specular test for evaluating high-gloss finishes, developed earlier at the duPont Company (Horning and Morse, 1947) and an 85° method for evaluating low-gloss, matte surfaces. The latter sheen method was developed in 1938 by J. W. Ayers of the C. K. Williams Company (Ayers, 1938; Hunter, 1952) and was subsequently used to test matte camouflage finishes used by the Ordinance Department. It is now used for measuring flat Interior wall paints, and low-gloss exterior painted aluminum siding.

A two-parameter method for 60° specular gloss designed to distinguish the image-forming gloss surface of nonmetals from nonimage-forming gloss surfaces was adopted as ASTM Method D1471 in 1969 (Nimeroff, 1957). It was designed to cover those cases in which measurements made by the ASTM Method D523 60 gloss method did not correlate with gloss appearance. Method D1471 specifies a second, two-receiver aperture, to be used in conjunction with the aperture of Method D523. An evaluation is then made of the amount of light received by each of the apertures.

In 1937, th e paper industry adopted a 75° specular-gloss method because the angle gave the best separation of coated book papers (Institute of Paper Chemistry, 1937; Hunter 1958). This method was adopted in 1951 by the Technical Association of Pulp and Paper industries as TAPPI Method T480. For the evaluation of waxed, lacquered, and cast-coated high-gloss papers at 20°, TAPPI Method T653 was adopted in 1958 with window angular sizes different from those of the 20 ASTM paint method (Hunter and Lofland, 1956).

SUMMARY OF THE INVENTION

Conventional gloss-meters and gloss-measurements suffer from a number of inherent drawbacks. Amongst these there may be mentioned the high resolving power of the human eye, compared with that of most reflectance measuring means. Most existing instruments provide scanty reliable information on the gloss of curved objects. The novel gloss-meter overcomes to a large extent the drawbacks of conventional instruments.

According to the present invention there is provided a versatile gloss-meter which is suitable for measuring gloss of flat as well as curved surfaces and bodies. Examples of produce the gloss of which can be determined in an objective manner, are fruit and certain types of vegetables.

The novel instrument is based on specific illumination means, which allows to change the angle of the light beam incident on the object during measurement.

Furthermore, means are provided for obtaining exact values of light reflected by the object and scattered by same over a wide solid angle. Means are also provided for scanning effectively a wide range of spatial angle for reflected and scattered light. Last not least, means are provided for the rapid and exact evaluation of the measured parameters, giving a quantititive indication of the gloss of the measured object and if desired, of other parameters of such an object. A variety of light sources can be used for creating the light beam by which the object is illuminated. According to preferred embodiment a narrow monochromatic light beam, such as from a suitable laser, is used for illumination.

Scattered and reflected light reaches an array of photosensitive elements, preferably arranged on an arc or part of arc, at a certain distance from the object, so that the photosensitive elements are at about the same distance from the measured object.

Increased sensitivity and capability of spatial resolution results from the use of a large number of such elements, each of a rather small surface area. Instead of such an array there may be used a video camera, preferably arranged in a movable manner so as to be able to scan a large spatial angle.

According to another embodiment, the object can be illuminated from a certain angle of incidence, and light coming from it can be collected on a half-transparent screen, which can be scanned so as to determine light intensity distribution over its surface. According to one embodiment of the invention, there are used two arrays of photo-sensitive elements, such as photodiodes or the like, which are arranged on two arcs, one preferably in the reflection plane and the other at 90° thereto, also on an arc. Generally the maximum of light intensity is found somewhere on the first arc, and this value can be taken as reference point for the calculation of gloss, obtained by dividing such maximum value by the discrete values at different points of the arc.

The measurement of gloss can be effected using a number of alternatives:

1. The object is stationary, generally in a suitable shallow hole, it is illuminated by a light source (generally a laser beam), which illuminates the object either at a given angle, or the angle of illumination which can be varied from horizontal to 90° elevation. There are provided two arches which support a large number of photosensitive elements, and which receive the light reflected or scattered from the object. The arches are stationary.

2. There can be provided a system where the illumination is either at a given angle, or which can be varied as regards angle with the horizontal plane, while illuminates the object, there is provided a system where the angle of the beam of light incident on the object can be varied.

3. An array of photosensitive elements can be arranged on a quarter-arch; this can be moved in a plane vertical to the support surface so as to scan any desired angle; generally a quarter of the circle, i.e. 90° will be sufficient.

The measurement can be made with a stationary light source at a given elevation; or measurements can be repeated with the light source at different angles.

4. There can be arranged a translucent screen above the object, which will generally be flat, the light source is used to illuminate the object at one or more angles of elevation, and there results an uneven illumination of the translucent screen, which is scanned by means of a CCD or similar means.

5. An array of photosensitive elements can be arranged in one or more arches; a source of a light beam can be provided either at a fixed elevation or at elevations which can be changed to predetermined values; the object is arranged on a rotatable support, so that when this rotates the entire visible surface of the object will be illuminated and light coming from its surface will be evaluated.

DESCRIPTION OF PREFERRED EMBODIMENT

A number of alternative embodiments of the invention are illustrated with reference to the enclosed schematical Figures, which are not according to scale, and in which.

Figure 1:
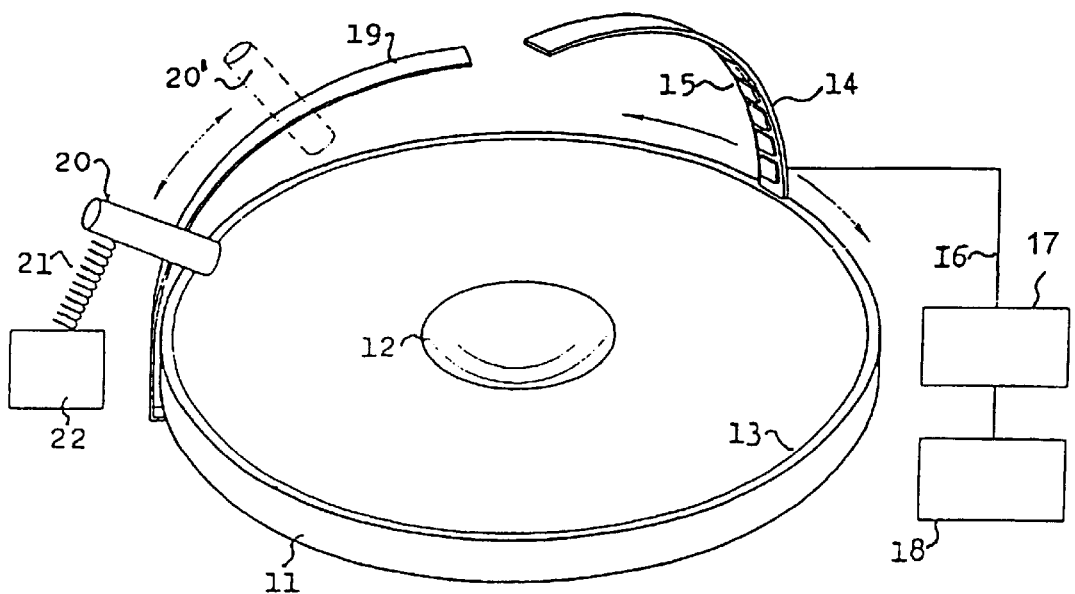
FIG. 1 is a perspective view of one glossmeter of the invention.

As shown in FIG. 1, the glossmeter illustrated comprises in combination a supporting plate 11, with a central recess 12 which serves to hold the body to be examined. Around plate 11 there is provided a rail-like structure 13 which supports arch 14, at the inside of which, facing recess 12, there are provided a plurality of photosensitive elements 15, such as photodiodes or the like, which are connected via cable 16 to amplifier 17 and to evaluation means 18. There is provided a second arch 19, on which there is slidingly arranged a light source 20, such as a laser with optical system to provide a light beam, directed at the object at the center of the plate 11. Two positions of the light source 20 are shown, 20 and 20'. The light source can be moved so as to make with the surface of support 11 an angle from above 0° to 90°. This light source is connected with flexible cable 21 connected with power source 22.

A device of this type can be used with a stationary arch 14 and in this case the photoelements will register the light coming from the object at the center of the plate 11.

The embodiment where the arch 14 can be moved along the perimeter of the plate 11 has the advantage that the light coming from various parts of the surface of the object is evaluated. Another possible embodiment, not shown, is an arrangement where there is provided at the center of the plate 11, a rotatable support, which can be rotated with the object supported by it, so as to scan the surface of the object.

Figure 2:
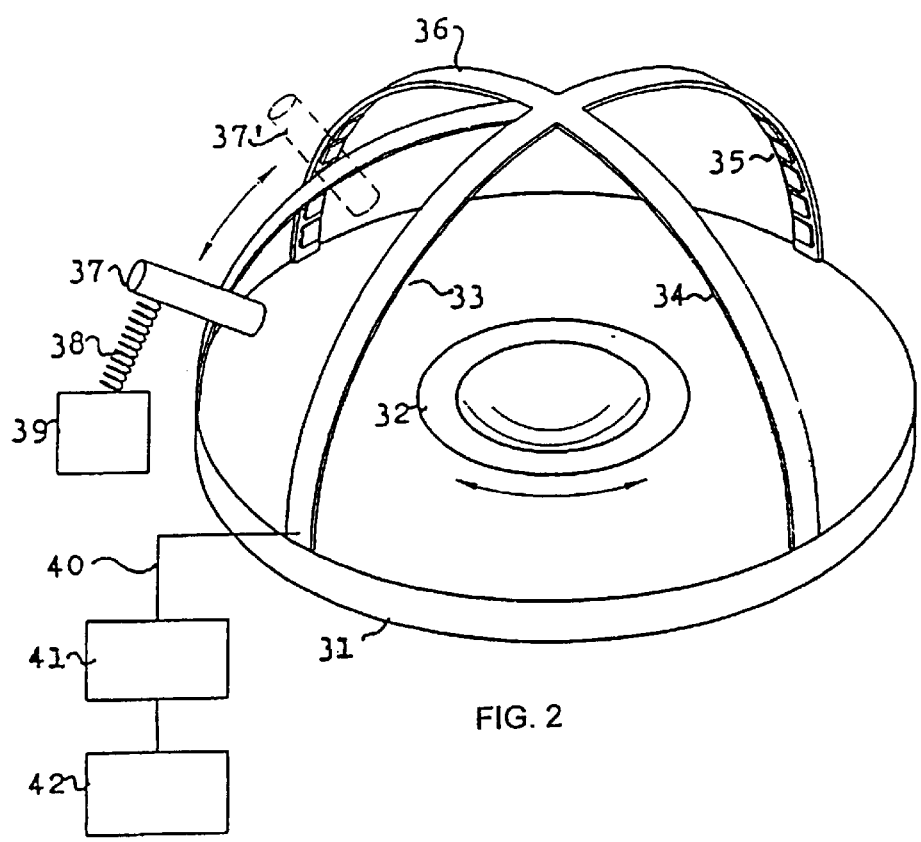
FIG. 2 is a perspective view of another embodiment of the invention.

Another embodiment is illustrated in FIG. 2, which comprises in combination a support plate 31, provided at its center with a rotatable support 32, which supports the object which is to be examined. There are provided two arches, 33 and 34, at the interior surface of which, facing the object, there are provided a plurality of photosensors, such as photodiodes 35. There is provided another arch 36, which supports the light source 37, which emits a beam directed at the object. This is advantageously a laser, and this is arranged on said arch 36 so as to make different angles with the surface of the plate 31. The rotating object and the variable-angle laser beam enable a thorough illumination of the surface of the object and a thorough evaluation of the gloss of the object.

The laser 37 is connected via cable 38 to power source 39 and the output of photosensors 35 passes via cable 40 to amplifying means 41, which is connected with evaluation means 42.

EXAMPLE 1

Figure 3:
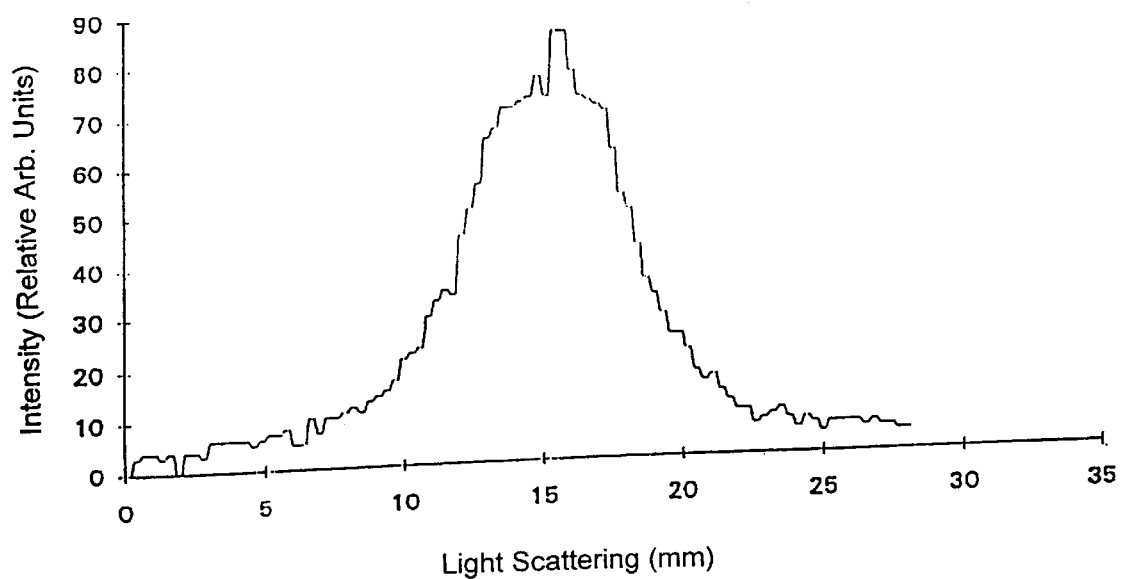
FIG. 3 is a graph of light scattering recorded by the glossmeter.

Ripe tomatos, of the Rehovot 175 strain, were placed in the glossmeter of the invention, and illuminated by a light beam from a helium-neon laser, at an angle of 45° with the horizontal supporting plate. The light was reflected on a translucent polypropylene screen arranged parallel to the supporting plate, and at an adequate distance from this. The light signals were picked up by an array of image analyzers by means of a suitable video-computer card, and the data were processed by a 486-IBM compatible computer. The results call be obtained in a graph of arbitrary relative values, as shown in enclosed FIG. 3 against light scattering in mm. The enclosed graph is that obtained with a certain specific tomato.

The picture is evaluated by two routes by measuring the fit with a distribution curve and determination of the relevant parameters, as well as by establishing a numerical value which characterizes a certain examined item. Every item, sucti as fruit, vegetable or the like, has to be tested in various positions, at least six, with one from each side, so as to obtain a more representative value as to its overall gloss.

The glossmeter according to the present invention was used to measure curved surfaces of Dwarf Cavendish Bananas. It was found that the ripening of the bananas was accompanied by a gradual decrease in gloss, which also correlated well with certain chemical and physical changes in the bananas. The change of gloss correlated well with changes of peel color and thus can be used to evaluate ripeness of bananas. The illumination was by a helium-neon laser light beam.

The angle of incidence of the laser beam on the banana peel was 45°.

Further experiments were carried out with eggplants, mature green tomatoes and apples. The average readings with the novel glossmeter were 9.5, 7.4 and 6.3 arbitrary GU units from eggplants, tomatoes and apples, respectively.

EXAMPLE 2

Commercially mature apples of the cultivar "Granny Smith" were obtained from a local orchard. All tests were undertaken within 2 hours of harvest to eliminate any possible post harvest deterioration.

Gloss Measurements

The fruits were positioned in the glossmeter and illuminated by a light beam from a helium-neon laser at an angle of 60° to a plane perpendicular to the surface. A semiconductive plate collected all reflected light from the surface of the fruits and a VCR camera (Sony, Japan), positioned directly facing the plate, recorded the images. The recorded images were relayed to a computer, where they were analyzed by a specially designed computer program, which translated them into the curvee form of light intensity (arbitrary units) Vs distance or light scattering (pixels). With the curved surface glossmeter, a low value indicated high gloss and vice-versa.

Gloss measurements for "Granny Smith" apples indicate that these were the least glossy of the fruits examined, with measurements of 96.3 pixels +/−4.8 obtained for the curved surface glossmeters.

EXAMPLE 3

Eggplants were examined. These are the most glossy of the fruits examined, with readings of 34.9 pixels +/−4.8 given by the curved surface glossmeters. It may be assumed that the very glossy appearance of the eggplant is due to a very effective light scattering wax layer covering the peel.

Gloss measurements of the mature eggplants following wax extraction indicate that lack of wax results in a lower gloss. Results of 40.5 pixels +/−1.8 were obtained using the curved surface glossmeters.

Mature green "Daniella 144" tomatoes exhibited curve gloss values of 61.9 pixels +/−10.9, indicating they were slightly less glossy than the eggplant and yet more glossy than the apples.

EXAMPLE 4

Marble was polished to three different degrees of smoothness, and its gloss was measured at each of these stages. Pronounced differences were found between the three degrees of polish, which were assigned the values "glossy", "matte" and "semi-glossy".

TABLE 1

| Types of gloss | Visual evaluation | Types of surfaces |
| --- | --- | --- |
| Specular gloss | Shininess, brilliance of highlights | medium-gloss surfaces of book paper, paint, plastics, etc. |
| Sheen | Shininess at grazing angles | Low-gloss surfaces of paint, paper, etc. |
| Contrast gloss or luster | Contrasst between specularly reflecting areas and other areas | Low-gloss surfaces of textile fiber, yarn and cloth, newsprint, bond paper, diffuse- |

TABLE 1-continued

| Types of gloss | Visual evaluation | Types of surfaces |
| --- | --- | --- |
| | | finish metals, hair, fur, etc. |
| Absence-of-bloom gloss | Absence of haze, or milky appearance, adjacent to reflected highlights | High and semi gloss surfaces in which reflected highlights may be seen |
| Distinctness-of image gloss | Distinctness and sharpness of mirror images | High-gloss surfaces of all types in which mirror images may be seen |
| Surface-uniformity gloss | Surface uniformity freedom from visible nonuniformities as seen in textures | Medium-to high-gloss surfaces of all types |

We claim:

1. A glossmeter providing detailed information on the gloss of an examined object, which comprises in combination means for holding the object with a substantial part of its surface exposed for examination, means for illuminating the object with a beam of light, and an array of photodetectors adapted to detect and measure light reflected and diffused from the surface of the object, where there is provided an array of photosensitive elements arranged at the inner surface of an arc defining a quarter of a circle, the apex of which is at the axis of the object and other end of which is located at the horizontal plane supporting the object, where means are provided for rotating the arc respective the object by an angle from 90° to 360° respective the verticle axis.

2. A glossmeter according to claim 1 where the light source is a laser, the beam of which can be directed at the object either at a fixed angle of incidence, or which can be directed at the object at any predetermined angle between nearly horizontal and up to perpendicular with the supporting surface.

3. A glossmeter providing detailed information on the gloss of an examined object, which comprises in combination means for holding the object with a substantial part of its surface exposed for examination, means for illuminating the object with a beam of light, and an array of photodetectors adapted to detect and measure light reflected and diffused from the surface of the object, where there are provided two arcs, of 180° each perpendicular with each other, with an array of photosensitive elements adjacent each other arranged on the surface of the arcs facing the object, means being provided for evaluating the signals from said elements, there being provided a laser for illuminating the object at an angle variable at will, with a monochromatic beam of light.

4. A glossmeter according to claim 3 where the light source is a laser, the beam of which can be directed at the object either at a fixed angle of incidence, or which can be directed at the object at any predetermined angle between nearly horizontal and up to perpendicular with the supporting surface.

* * * * *

UNITED STATES PATENT AND TRADEMARK OFFICE
Certificate

Patent No. 6,018,396

Patented: January 25, 2000

On petition requesting issuance of a certificate for correction of inventorship pursuant to 35 U.S.C. 256, it has been found that the above-identified patent, through error and without deceptive intent, improperly sets forth the inventorship.

Accordingly, it is hereby certified that the correct inventorship of this patent is: Amos Nussinovitch, Petach Tikva, Israel and Eyal Mey-Tal, Rehovot, Israel.

Signed and Sealed this Second Day of October 2001.

FRANK G. FONT
*Supervisory Patent Examiner*
Art Unit 2877